United States Patent [19]

Goldmann et al.

[11] Patent Number: 4,895,855
[45] Date of Patent: Jan. 23, 1990

[54] MIXTURE OF DIFFERENT DIHYDROPYRIDINES

[75] Inventors: Siegfried Goldmann, Wuppertal; Horst Böshagen, Haan; Friedrich Bossert, Wuppertal; Gerhard Franckowiak, Wuppertal; Horst Meyer, Wuppertal; Jürgen Stoltefuss, Haan; Rainer Gross, Wuppertal; Matthias Schramm, Cologne; Günter Thomas, Wuppertal, all of Fed. Rep. of Germany

[73] Assignee: Bayer Aktiengesellschaft, Leverkusen, Fed. Rep. of Germany

[21] Appl. No.: 806,160

[22] Filed: Dec. 6, 1985

[30] Foreign Application Priority Data

Dec. 22, 1984 [DE] Fed. Rep. of Germany ....... 3447170

[51] Int. Cl.$^4$ ............................................. A61K 31/44
[52] U.S. Cl. ..................... 514/302; 514/299; 514/301; 514/344; 514/350; 514/150; 514/352; 514/356
[58] Field of Search ..................... 514/352, 356, 302

[56] References Cited

U.S. PATENT DOCUMENTS

| | | | |
|---|---|---|---|
| 3,911,123 | 10/1975 | Meyer et al. | 514/352 |
| 3,932,646 | 1/1976 | Meyer et al. | 514/356 |
| 4,264,611 | 4/1981 | Berntsson et al. | 514/356 |
| 4,284,634 | 8/1981 | Satu | 514/352 |
| 4,582,840 | 4/1986 | Garthoff et al. | 514/356 |
| 4,675,329 | 6/1987 | Wehinger et al. | 514/356 |
| 4,764,516 | 8/1988 | Franckowiak et al. | 514/352 |

FOREIGN PATENT DOCUMENTS

| | | | |
|---|---|---|---|
| 169470 | 1/1986 | European Pat. Off. | 514/356 |
| 207674 | 1/1987 | European Pat. Off. | 514/352 |
| 2752820 | 5/1979 | Fed. Rep. of Germany | 514/352 |
| 3317872 | 11/1984 | Fed. Rep. of Germany | 514/356 |
| 3419131 | 11/1985 | Fed. Rep. of Germany | 514/356 |
| 55-85563 | 6/1980 | Japan | 514/356 |

Primary Examiner—Frederick E. Waddell
Attorney, Agent, or Firm—Sprung Horn Kramer & Woods

[57] ABSTRACT

A composition effective for treating circulation disorders comprises a mixture of

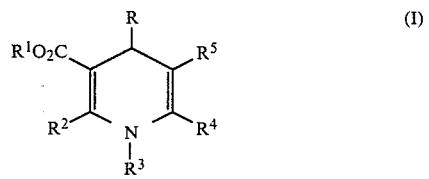

and

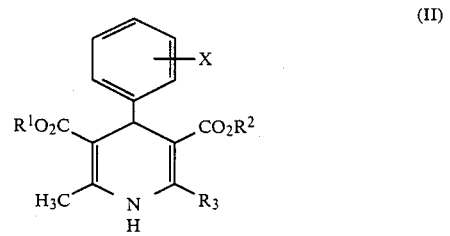

wherein the variables can have varied meetings. I are inotropic and II are vasodilating but, whereas the ingredients in the combination would be expected to be antagonistic, they are reinforcing.

2 Claims, No Drawings

MIXTURE OF DIFFERENT DIHYDROPYRIDINES

The invention relates to an active compound combination having a positive inotropic and anti-anginal activity containing positive inotropic dihydropyridines (component A) and vasodilating dihydropryridines (component B), to processes for the preparation thereof and to the use thereof in medicaments.

As positive inotropic dihydropyridines (component A), those of the following formula (I) may be mentioned

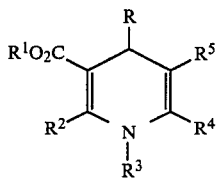

in which
R represents cycloalkyl ($C_3$-$C_{14}$) or
represents aryl ($C_6$-$C_{14}$) or heteroaryl which are optionally substituted by up to five identical or different substituents from the series: halogen, nitro, cyano, trifluoromethyl, monofluoroalkoxy ($C_1$-$C_{12}$), polyfluoroalkoxy ($C_1$-$C_{12}$), hydroxyl, amino, alkylamino, dialkylamino (alkyl $C_1$-$C_8$ in each case), aryl ($C_6$-$C_{14}$), heteroaryl, aralkyl ($C_7$-$C_{14}$), —O—aralkyl ($C_7$-$C_{14}$) or —$SO_n$— aralkyl ($C_7$-$C_{14}$; n=0-2), it being possible for substituents of the five last-mentioned groups also to be polysubstituted by up to five substituents from the series: halogen, nitro, azido, hydroxyl, trifluoromethyl, trifluoromethoxy, cyano, amino, alkylamino, dialkylamino (alkyl $C_1$-$C_8$ in each case), alkoxy alkylthio (alkyl $C_1$-$C_4$ in each case), $R^1$ represents a straight-chain, branched or cyclic, saturated or unsaturated hydrocarbon radical (up to $C_{20}$) which is optionally interrupted by up to five sulphur and/or oxygen atoms in the chain and is optionally substituted by halogen, nitro, hydroxyl, cyano, trialkylsilyl (alkyl $C_1$-$C_8$ in each case), alkoxycarbonyl ($C_1$-$C_4$), amino, alkylamino or dialkylamino (alkyl $C_1$-$C_4$ in each case), $R^2$, $R^4$—are identical or different and represents
hydrogen,
amino,
cyano,
formyl or
straight-chain, branched or cyclic alkyl or alkenyl (up to $C_{10}$) each of which is optionally substituted by hydroxyl, carboxyl, alkoxycarbonyl ($C_1$-$C_4$) or halogen, $R^3$ represents hydrogen or
straight-chain, branched or cyclic alkyl or alkenyl (up to $C_{10}$) each of which is optionally substituted by halogen, cyano, hydroxyl, amino, alkylamino, dialkylamino (alkyl $C_1$-$C_4$ in each case) or by a 5-membered to 7-membered heterocyclic ring which can contain nitrogen and/or oxygen and/or sulphur as the heteroatoms and can be either saturated or unsaturated, and $R^5$ represents hydrogen,
cyano or
nitro or $R^4$ and $R^5$ together form a ring such as

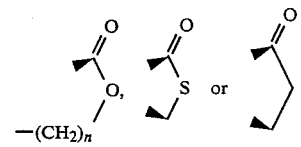

n representing 1 or 2.

Preferred compounds of the general formula (I) are those in which
R represents cycloalkyl ($C_4$-$C_{12}$) or
represents phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazoyl, quinoxalyl, thionaphthenyl, isothionaphthenyl, chromonyl, thiochromonyl, chromenyl, thiochromenyl, benzoxadiazolyl or benzthiadiazolyl, it being possible for the said radicals to be optionally substituted by up to 4 identical or different substituents from the series: fluoro, chloro, bromo, iodo, nitro, cyano, trifluoromethyl, monofluoroalkoxy ($C_1$-$C_8$), polyfluoroalkoxy ($C_1$-$C_8$), hydroxyl, amino, alkylamino, dialkylamino (alkyl $C_1$-$C_6$ in each case), phenyl, naphthyl, thienyl, furyl, pyridyl, pyrimidyl, benzyl, —O—benzyl, —$SO_n$— benzyl (n=0-2), it being possible for the aromatics and hetero-aromatics in turn to be optionally mono-substituted to tetrasubstituted by fluoro, chloro, bromo, iodo, cyano, nitro, azido, hydroxyl, trifluoromethyl, trifluoromethoxy, amino, alkylamino, dialkylamino, (alkyl $C_1$-$C_6$ in each case), alkoxy or alkylthio ($C_1$-$C_2$ in each case)

$R^1$ represents a straight-chain, branched or cyclic saturated or unsaturated hydrocarbon radical (up to $C_{17}$) which is optionally interrupted in the chain by up to 4 oxygen and/or sulphur atoms and is optionally monosubstituted or polysubstituted by fluoro, chloro, bromo, iodo, nitro, hydroxyl, cyano, trialkylsilyl ($C_1$-$C_6$), alkoxycarbonyl ($C_1$-$C_2$), amino, alkylamino or dialkylamino (alkyl $C_1$-$C_2$ in each case), $R^2$, $R^4$—are identical or different and represents
hydrogen,
amino,
cyano,
formyl or
straight-chain, branched or cyclic alkyl or alkenyl (up to $C_8$) each of which is optionally substituted by hydroxyl, carboxyl, alkoxycarbonyl ($C_1$-$C_2$), or one or more of fluoro, chloro or bromo, $R^3$—represents hydrogen or
straight-chain, branched or cyclic alkyl or alkenyl (up to $C_8$) each of which is optionally interrupted in the chain by up to 3 oxygen atoms and is optionally monosubstituted or polysubstituted by fluoro, chloro, bromo, iodo, cyano, hydroxyl, amino, alkylamino, dialkylamino (alkyl $C_1$-$C_2$ in each case), morpholine, piperidine, pyridazine or pyridine, and $R^5$—represents hydrogen,
cyano or
nitro, or
$R^4$ and $R^5$ together form a ring such as

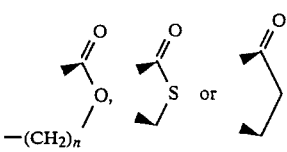

n representing 1 or 2.

Particularly preferred are compounds of the formula (I) in which

R represents cycloalkyl ($C_5-C_{10}$) or
  phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinazolyl, quinoxalyl, thionaphthenyl, isothionaphthenyl, chromonyl, thiochromonyl, chromenyl, thiochromenyl, benzoxadiazolyl or benzthiadiazolyl, the said radicals being optionally substituted by up to three identical or different substituents from the series: fluoro, chloro, bromo, nitro, cyano, trifluoromethyl, monofluoroalkoxy ($C_1-C_4$), polyfluoroalkoxy ($C_1-C_4$), hydroxyl, amino, alkylamino, dialkylamino (alkyl $C_1-C_4$ in each case), phenyl, thienyl, pyridyl, benzyl, —O-benzyl or —$SO_n$-benzyl (n=0 to 2), it being possible for the aromatics and heteroaromatics in turn to be optionally monosubstituted to trisubstituted by fluoro, chloro, bromo, cyano, nitro, hydroxyl, trifluoromethyl, trifluoromethoxy, amino, alkylamino, dialkylamino (alkyl $C_1-C_4$ in each case), methoxy or methylthio, $R^1$ represents a straight-chain, branched or cyclic, saturated or unsaturated hydrocarbon radical (up to $C_{14}$) which can optionally be interrupted by up to three oxygen and/or sulphur atoms in the chain and is optionally monosubstituted or polysubstituted by fluoro, chloro, bromo, nitro, hydroxyl, cyano or trialkylsilyl ($C_1-C_4$), $R^2$, $R^4$ are identical or different and represents
  hydrogen,
  amino,
  cyano,
  formyl or
  straight-chain or branched alkyl or alkenyl (up to $C_6$) each of which is optionally substituted by hydroxyl, $R^3$ represents hydrogen or
  straight-chain, branched or cyclic alkyl or alkenyl (up to $C_6$) each of which is optionally interrupted by up to two oxygen atoms in the chain and is optionally monosubstituted or polysubstituted by fluoro, chloro, cyano, hydroxyl, amino or morpholino, and $R^5$ represents hydrogen,
  cyano or
  nitro, or $R^4$ and $R^5$ together form a ring such as:

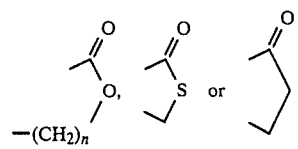

n representing 1 or 2.

The following may be mentioned especially: Methyl 1,4-dihydro-2,6-dimethyl-5-nitro-4-(2-trifluoromethyl-phenyl)-pyridine-3 carboxylate (BAY K 8644) and ethyl 2-methyl-4-(4-oxo-2-phenyl-4H-thiochromen-8-yl)-5-oxo-1,4,5,7-tetrahydrofuro[3,4-b]pyridine-3-carboxylic ethylester.

The preparation of these compounds has been described in DE-OS (German Published Specifications) 3,206,671, 3,311,005 and 3,311,003.

As the vasodilating dihydropyridines (component B), those of the following formula (II) may be mentioned,

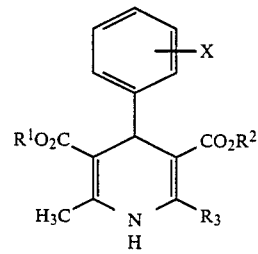

in which
  $R^1$ represents alkyl ($C_1-C_4$) optionally substituted by alkoxy ($C_1-C_3$),
  $R^2$ represents alkyl ($C_1-C_{10}$) optionally substituted by alkoxy ($C_1-C_3$), trifluoromethyl, trifluoroethyl or N-methyl-N-benzylamino,
  $R^3$ represents cyano,
    hydroxymethyl or
    alkyl ($C_1-C_4$), and
  X represents 2-nitro, 3-nitro, 2-chloro, 2,3-dichloro or a 2,3-ring member consisting of =N—O—N=.

The compounds in the table which follows are particularly preferred:

TABLE

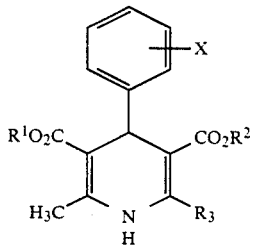

| No. | X | $R^1$ | $R^2$ | $R^3$ | generic |
|---|---|---|---|---|---|
| 1 | 2-$NO_2$ | $CH_3$ | $CH_3$ | $CH_3$ | Nifedipine |
| 2 | 3-$NO_2$ | $nPrOCH_2CH_2$ | $nPrOCH_2CH_2$ | $CH_3$ | Niludipine |
| 3 | 3-$NO_2$ | $C_2H_5$ | $CH_3$ | $CH_3$ | Nitrendipine |

TABLE-continued

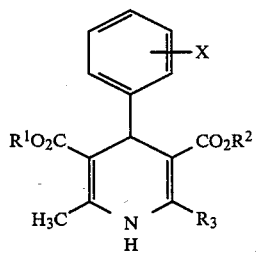

| No. | X | R¹ | R² | R³ | generic |
|---|---|---|---|---|---|
| 4 | 2-NO₂ | CH₃ | (CH₃)₂CHCH₂ | CH₃ | Nisoldipine |
| 5 | 3-NO₂ | CH(CH₃)₂ | (CH₂)₂—O—CH₃ | CH₃ | Nimodipine |
| 6 | 3-NO₂ | C₂H₅ | C₁₀H₂₁(n) | CH₃ | |
| 7 | 2-Cl | CH₃ | CH₂—CF₃ | CH₃ | |
| 8 | 2-Cl | C₂H₅ | CH₂—CF₃ | CH₃ | |
| 9 | 3-NO₂ | CH(CH₃)₂ | n-Pro—CH₂CH₂ | CH₃ | |
| 10 | 3-NO₂ | CH₃ | C₆H₅CH₂N(CH₃)CH₂CH₂ | CH₃ | Nicardipine |
| 11 | 2,3-Cl₂ | C₂H₅ | CH₃ | CH₃ | Felodipine |
| 12 | 2,3═N—O—N═ | C₂H₅ | C₂H₅ | CH₃ | Dazodipine |
| 13 | 2,3═N—O—N═ | CH₃ | CH(CH₃)₂ | CH₃ | (PN 200–110) |
| 14 | 3-NO₂ | C₂H₅ | C₂H₅ | CH₂OH | |
| 15 | 3-NO₂ | CH₃ | CH₃ | CN | Nivadipine | n-Pr = n-Propyl

Nitrendipine, nicardipine, nisoldipine, felodipine, nifedipine, nimodipine, the product No. 13 in the table and dazodipine may be mentioned in particular. The preparation of these compounds is described in U.S. Patent Specification No. 3,485,847, European Patent Specification 7,293, DOS (German Published Specification) 2,407,115, DOS (German Published Specification) 2,549,568, DOS (German Published Specification) 2,117,571, DOS (German Published Specification) 2,949,464 and DOS (German Published Specification) 2,949,491.

Since both calcium-antangonistic and positive inotropic dihydropyridines are bound to the same receptor, only a weakening of the individual activity would be expected for the combination of the two components.

However, under suitable conditions, the combination of the components A and B shows a completely surprising activity pattern: it is positive inotropic and vasodilating, in particular coronary-dilating.

Relative to 1 to 10 parts by weight of component A, 0.1 to 100 parts by weight, preferably 0.1 to 10 parts by weight, of component B can be employed.

The invention also relates to combinations of positive inotropic, racemic dihydropyridines with vasodilating, optically active dihydropyridines, combinations of vasodilating, racemic dihydropyridines with positive inotropic, optically active dihydropyridines, and to combinations of optically active, positive inotropic dihydropyridines with optically active, vasodilating dihydropyridines.

The combination can be prepared by dissolving the individual components in inert solvents in which these are soluble, and mixing these solutions in the appropriate quantitative ratios.

Alcohols, such as ethanol, or glycols, such as polyethylene glycol, and in particular dimethyl sulphoxide may be mentioned by way of example as inert solvents. As already mentioned, the combination according to the invention can be employed for the control of disease, especially circulatory and heart diseases, e.g. ischaemic heart diseases, heart failure or hypertension.

The active compound combination can be converted in a known manner into the customary formulations, such as tablets, capsules, dragees, pills, granules, aerosols, syrups, emulsions, suspensions and solutions, using inert non-toxic, pharmaceutically suitable excipients or solvents. The therapeutically active compounds should in each case be present in a concentration of about 0.01 to 90% by weight of the total mixture, that is to say in amounts which suffice to achieve the dosage range indicated.

These formulations are prepared, for example, by extending the active compound combination with solvents and/or excipients, optionally with the use of emulsifiers and/or dispersing agents, and, for example when using water as a diluent, organic solvents can optionally be used as auxiliary solvents.

Examples of auxiliary substances which may be mentioned are:

Water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid excipients, such as, for example, natural rock powders (for example kaolins, aluminas, talc and chalk), synthetic rock powders (for example highly disperse silica and silicates) and sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral use, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium lauryl-sulphate and talc, can be co-used when making tablets. In the case of aqueous suspensions and/or elixirs which are intended for oral use, the active compound combinations can be mixed with various flavor-improving agents or colorants in addition to the abovementioned auxiliary substances.

In the case of parenteral use, solutions of the active compound combination, employing suitable liquid excipients, can be used.

The effects of the combinations according to the invention on the heart and vessels were detected on isolated perfused guinea pig hearts (modified according to Opie, L., J. Physiol. 180 (1965) 529–541). The hearts of albino guinea pigs of 250 to 350 g weight are used for this purpose. The animals are killed with a knock on the head, the thorax is opened, a metal cannula is tied into the exposed aorta and the left atrium is opened. The heart with the lungs is separated out of the thorax and connected via the aorta cannula to the perfusion apparatus, with perfusion running. The lungs are separated off at the lung roots. The perfusion medium used is Krebs-Henseleit solution (118.5 mmol/liter of NaCl, 4.75 mmol liter of KCl, 1.19 mmol/liter of $MgSO_4$, 25 mmol/liter of $NaHCO_3$, 0.013 mmol/liter of NA-EDTA), the $CaCl_2$ concentration of which is varied as required, but amounts as a rule to 1.2 mmol/liter. 10 mmol/liter of glucose are added as the enrgy-supplying substrate. Before the perfusion, the solution is filtered until free of particles. The solution is treated with Carbogen gas (95% of $O_2$, 5% of $CO_2$ for maintaining a pH value of 7.4). The hearts are perfused at a constant rate (10 ml/minute) at 32° C. by means of a peristaltic pump.

For measuring the heart function, a liquid-filled latex bag, which is connected via a liquid column to a pressure sensor, is introduced through the left artium into the left ventricle and the isovolumetric contractions are recorded on a high-speed recorder.

The perfusion pressure as a measure of the coronary resistance is recorded by means of a pressure sensor. Under these conditions, a fall in the perfusion pressure indicates a coronary dilatatation, and a rise in the pressure amplitude in the left ventricle indicates a rise in the heart contractility. The combinations according to the invention are infused in suitable dilutions into the perfusion system just before the isolated heart.

Thus, the combinations listed by way of example in the table which follows have a positively inotropic and coronary-dilating effect on the isolated perfused guinea pig heart.

| Combination | | (Percentage rise (+) or fall | |
|---|---|---|---|
| Component A | Component B | (−) as compared with the control) | |
| | | CA | PP |
| From combination 1 | | +38 | −18 |
| BAY K 8644:nifedipine (100 nmol/l) (100 nmol/l) | | | |
| From combination 2 | | +32 | −21 |
| BAY K 8644:nisoldipine (100 nmol/l) (100 nmol/l) | | | |
| From combination 3 | | +18 | −17 |
| BAY K 8644:nicardipine (100 nmol/l) (200 nmol/l) | | | |
| From combination 4 | | +47 | −24 |
| BAY K 8644:nitrendipine (30 nmol/l) (90 nmol/l) | | | |

CA = contraction amplitude
PP = perfusion pressure

The combinations 1 to 4 are prepared as follows:
Combination 1
Initially, $3.6 \times 10^{-3}$ g of BAY K 8644 are dissolved in one ml of DMSO, $3.5 \times 10^{-3}$ g of nifedipine, then dissolved in one ml of DMSO and subsequently the two solutions are mixed in a 1:1 ratio, and appropriate dilutions with 0.9% NaCl are made for infusion.
Combination 2
Initially, $3.6 \times 10^{-3}$ g of BAY K 8644 are dissolved in one ml of DMSO, $3.9 \times 10^{-3}$ of nisoldipine are then dissolved in one ml of DMSO and subsequently the two solutions are mixed in a 1:1 ratio, and appropriate dilutions with 0.9% NaCl are made for infusion.
Combination 3
Initially, $3.6 \times 10^{-3}$ g of BAY K 8644 are dissolved in one ml of DMSO, $9.3 \times 10^{-3}$ g of nicardipine are then dissolved in one ml of DMSO and subsequently the two solutions are mixed in a 1:1 ratio, and appropriate dilutions with 0.9% NaCl are made for infusion.
Combination 4
Initially, $1 \times 10^{-3}$ of BAY K 8644 are dissolved in one liter of DMSO, $3.2 \times 10^{-3}$ g of nitrendipine are then dissolved in one ml of DMSO and subsequently the two solutions are mixed in a 1:1 ratio, and appropriate dilutions with 0.9% NaCl are made for infusion.

It is understood that the specification and examples are illustrative but not limitative of the present invention and that other embodiments within the spirit and scope of the invention will suggest themselves to those skilled in the art.

We claim:

1. A vasodilating composition comprising (A) ethyl 2-methyl-4-(4-oxo-2-phenyl-4H-thiochromen-8-yl)-5-oxo-1,4,5,7-tetrahydrofuro(3,4-b)pyridine-3-carboxylic ethylester and (B) at least one member selected from the group consisting of nitrendipine, nicardipine, nisoldipine and nifedipine, there being present 50 to 200 nmols of (B) per mol of (A).

2. A method of treating a circulation disorder in a patient which comprises administering to such patient a circulation active effective amount of a composition according to claim 1.

* * * * *